United States Patent [19]

Lloyd et al.

[11] 4,410,627

[45] Oct. 18, 1983

[54] GLUCOSE ISOMERASE PROCESS

[75] Inventors: Norman E. Lloyd, Clinton, Iowa; Robert O. Horwath, Westport, Conn.

[73] Assignee: Nabisco Brands, Inc., Parsippany, N.J.

[21] Appl. No.: 393,848

[22] Filed: Jun. 30, 1982

[51] Int. Cl.³ .............................................. C12P 19/24
[52] U.S. Cl. ..................................................... 435/94
[58] Field of Search .................................. 435/94, 234

[56] References Cited

U.S. PATENT DOCUMENTS

| | | | |
|---|---|---|---|
| 3,826,714 | 7/1974 | Suekane et al. | 435/94 |
| 4,025,389 | 5/1977 | Poulsen et al. | 435/94 |
| 4,276,379 | 6/1981 | Heady | 435/94 |
| 4,284,722 | 8/1981 | Tamuri et al. | 435/94 |
| 4,308,349 | 12/1981 | Foley et al. | 435/94 |
| 4,310,628 | 1/1982 | Leiser | 435/94 |
| 4,348,480 | 9/1982 | Brownewell | 435/234 |

*Primary Examiner*—Lionel M. Shapiro
*Attorney, Agent, or Firm*—Richard Kornutik

[57] ABSTRACT

A process is provided for the enzymatic isomerization of a glucose-containing liquor to provide a high quality glucose-fructose syrup of from about 53 to about 60 weight percent fructose based on the glucose of the original feed without the need for fractionation and recycle operations. The process features careful adjustment of original glucose concentration, pH and contact times of glucose with glucose isomerase at a temperature of 90° C. to 130° C. to attain high fructose content without the formation of undue amounts of psicose and sugar degradation products.

39 Claims, No Drawings

GLUCOSE ISOMERASE PROCESS

BACKGROUND OF THE INVENTION

This invention relates to an enzymatic process for converting glucose (dextrose) to fructose (levulose).

Most food grade glucose is provided as an enzymatic hydrolysate of corn starch, i.e., the corn syrup of commerce. Glucose is generally rated at being 60 to 80% as sweet as sucrose and therefore sells at a correspondingly lower price. In order to bring the sweetness level of glucose up to that of the more expensive sucrose, it has long been known to isomerize glucose to fructose (which is even sweeter than sucrose) employing an enzyme having glucose isomerase activity, preferably one which has been immobilized upon an inert support such as diethylaminoethyl-cellulose, or porous glass. Detailed descriptions of the enzymatic conversion of glucose to fructose employing glucose isomerase can be found in Hamilton, et al. "Glucose Isomerase a Case Study of Enzyme-Catalyzed Process Technology", *Immobilized Enzymes in Food and Microbial Processes*, Olson et al., Plenum Press, New York, (1974), pp. 94–106, 112, 115–137; Antrim, et al., "Glucose Isomerase Production of High-Fructose Syrups", *Applied Biochemistry and Bioengineering*, Vol. 2, Academic Press (1979); Chen, et al., "Glucose Isomerase (a Review)", *Process Biochem.*, (1980), pp. 30–35; Chen, et al. "Glucose Isomerase (a Review)", *Process Biochem.*, (1980), pp. 36–41; Nordahl, et al., "Fructose Manufacture from Glucose by Immobilized Glucose Isomerase", *Chem. Abstracts*, Vol. 82, (1975), Abs. No. 110316h; and Takasaki, "Fructose Production by Glucose Isomerase", *Chem Abstracts*, Vol. 81, (1974), Abs. No. 7647a. In addition, there are numerous patents relating to glucose isomerization of which U.S. Pat. Nos. 3,616,221; Re. 28,885 (originally 3,623,953); 3,694,313; 3,708,397; 3,715,276; 3,788,945; 3,826,714; 3,843,442; 3,909,354; 3,960,663; 4,144,127; and, 4,308,349 are representative.

The levels of fructose achievable by the isomerization of glucose syrups with glucose isomerase is limited by the equilibrium of the isomerase reaction. At 65° C., the equilibrium of the reaction stands at approximately 51% fructose by weight from a starting substrate of pure dextrose. When refined dextrose liquor is used as the substrate (containing up to about 6% nonmonosaccharides by weight) and allowing for a reasonable residence time in the enzyme reactor, an approximately 50% fructose syrup is the highest fructose content which can be obtained (on a dry basis) by the prior procedures referred to. To attain syrups of higher fructose content, fractionation systems must be employed which add greatly to the cost of the final product. At higher temperatures, however, the equilibrium becomes more favorable. For example, an enzymatic glucose isomerase process capable of being operated at temperatures of from about 90°–130° C. could be used to directly provide high fructose corn syrups (HFCS) containing 53–60 weight percent fructose on a dry basis thereby eliminating the need for fractionation and recycle. However, the tendency of known glucose isomerase systems to undergo thermal denaturation with an accompanying sharp reduction in activity has thus far frustrated attempts to utilize higher temperature regimes to force the equilibrium of the isomerization further in favor of fructose. Moreover, glucose and especially fructose are sensitive reducing sugars which have a marked tendency to form unwanted by products such as psicose, colored products, color precursors and acids when heated to the temperatures necessary to isomerize according to this invention.

SUMMARY OF THE INVENTION

It has now been surprisingly discovered that by carrying out a glucose isomerization procedure within certain critical limits of initial glucose concentration, pH and residence time in the enzyme reactor as hereinafter defined, isomerization temperatures of from abut 90° C. to about 130° C. can be effectively utilized to directly provide HFCS syrups of high quality containing from about 53 to about 60 weight percent fructose without incurring undue psicose formation or sugar degradation thereby eliminating the need for expensive and operationally complex fractionation and recycle operations which are reqired by known glucose isomerization processes to achieve HFCS syrups having the aforesaid range of fructose concentration.

In accordance with the present invention, glucose is isomerized to glucose-fructose syrup by the process which comprises contacting a glucose-containing liquor containing from about 20 to about 65 weight percent glucose with glucose isomerase at a temperature of from about 90° C. to about 130° C. at a pH of from about 3 to about 8 and a contact time of from about 10 seconds to about 5 hours to convert at least about 53 to about 60 weight percent of the glucose present in said liquor to fructose with formation of less than 1% psicose and increase in color of less than 20 (CIRF×100).

The foregoing process is not dependent upon the use of a particular glucose isomerase but can be carried out with a glucose isomerase which has sufficient stability to withstand inactivation at 90° C. and higher for a time to effect a sufficient degree of isomerisation as will be defined herein. It is, however, within the scope of the present invention to utilize a glucose isomerase particularly noted for its thermal stability, for example, glucose isomerase produced by *Bacillus stearothermophilus* as disclosed in U.S. Pat. No. 3,826,714 and glucose isomerase produced by microorganisms of the genus Ampullariella as disclosed in U.S. Pat. No. 4,308,349. In addition, thermally stable glucose isomerase can be obtained using *Bacillus licheniformis* as described in European Pat. Application No. 41,213 as well as using thermophiles of the genera Thermoactinomyces, Thermopolyspora, Thermomonospora, and Pseudonocardia as described in Japanese Patent Publication 74 305588 (C.A. 81; 76474a). Each of these references is incorporated herein by reference.

DESCRIPTION OF THE PREFERRED EMBODIMENT

The glucose which is isomerized to fructose in accordance with the present invention can be derived from any of the known sources for this sugar. For reasons of economy, the glucose will usually be derived from the hydrolysis of cellulose or starch employing acid and/or enzyme, preferably the latter, in accordance with known procedures. Glucose containing liquors obtained in this way will typically contain minor quantities of polysaccharides, sugar oligomers, etc., depending upon the carbohydrate source employed and the hydrolysis method utilized. Cereal grains such as corn, milo, wheat, rye, and the like, and amylaceous roots and tubers such as potatoes, yams, carrots, cassava (manioc), and the like, are excellent sources of starch for conversion to the glucose starting material of this invention. In the United States, corn starch is especially preferred due to its comparatively low cost and ready availability. Since the production of food grade glucose favors the use of enzymatic starch hydrolysis procedures, such procedures are preferred herein. Enzyme hydrolysis methods are described in U.S. Pat. Nos. 4,017,363, 3,912,590, 3,922,196, 3,922,197-201 and 4,284,722, the disclosures of which are incorporated by reference herein.

The glucose isomerase employed herein can be isolated from among any of the known glucose isomerase-producing microorganisms including Streptomyces flavorirens, Streptomyces achromogenes, Streptomyces echinatus, Streptomyces albus, Streptomyces wedmorensis, Streptomyces phaeochromogenes, Streptomyces bobiliae, Streptomyces olivochromogenes, Streptomyces venezuelae, Aerobacter aerogenes, Aerobacter cloacae, Bacillus coagulans, Bacillus megaterium, Bacillus fructosus, Brevibacterium pentaaminoacidicum, Escherichia intermedia, Leuconostoc mesenteroides, and *Paracolobactrum aerogenoides*. In addition, glucse isomerases elaborated by the genus Nocardia, Micromonospora, Microbispora, Microellobospora and Arthrobacter can be used. Streptomyces sp. ATCC 21,175 is an excellent source for glucose isomerase for use in the process of this invention. As previously stated, it can be advantageous to utilize glucose isomerase which possesses stability at the relatively high isomerization temperatures employed herein, e.g., glucose isomerase produced by *Bacillus stearothermophilus*, in particular, strains selected from the group consisting of *Bacillus stearothermophilus* ATCC 21,365, NRRL B-3680, NRRL B-3681 and NRRL B-3682 as disclosed in U.S. Pat. No. 3,826,714; glucose isomerase produced by a microorganism of the genus Ampullariella such as *Ampullariella digitata, Ampullariella lobata, Ampullariella campanulata* and *Ampullariella regularis* (U.S. Pat. No. 3,826,714); glucose isomerase produced by *Bacillus licheniformis* (European Patent Application No. 41213); and glucose isomerase produced by the thermophiles of the genera described in Japanese Patent Publication No. 74 30588.

In addition to the aforementioned microorganisms, the present invention contemplates the use of mutants and variants thereof as well as genetically transformed microorganisms derived therefrom by introduction of mutated glucose isomerase genes into other microorganisms, including mesophilic and preferably thermophilic microorganisms. The mutated glucose isomerase genes selected for such use are those which provide glucose isomerase which is stable at elevated temperatures, especially above 90° C. and preferably up to about 130° C. Such genes can be prepared by the usual techniques used for mutation of microorganisms such as irradiation or chemical means. Thus, isolated glucose isomerase genes which produce glucose isomerase of moderate thermal stability, as produced for example by certain Streptomyces strains, on in vitro mutagenesis will undergo mutation, and selection of the appropriate mutated genes is accomplished by reintroduction of the mutated gene into either the parent or other organism, preferably a thermophilic organism, followed by replication of the organism and testing of the thermal stability of the resulting glucose isomerase.

Since glucose isomerase is produced intracellularly by these and other microorganisms, a source of glucose isomerase can be provided by simply harvesting the cells. The glucose isomerase can be separated from the cells by techniques known in the art, eg., sonic disruption, and employed in an enzyme reactor of known and conventional design. Preferably, the glucose isomerase employed herein, regardless of its source, will be immobilized on an inert substrate in accordance with known and conventional procedures. Materials and procedures used for the immobilization of enzymes are well known and are described in a number of publications including Wang, et al., *Fermentation & Enzyme Technology*, John Wiley & Sons, Inc., New York (1979), pp. 318–338 and Kirk-Othmer, *Encyclopedia of Chemical Technology*, 3rd Ed., John Wiley & Sons, Inc., New York (1980) Vol. 9 pp. 148–172, the disclosures of which are incorporated by reference herein. The presence of small quantities of cobalt, manganese and magnesium cation and/or water soluble salt of sulfurous acid such as sodium sulfite, sodium bisulfite, magnesium sulfite, and/or magnesium bisulfite as taught in U.S. Pat. No. Re. 28,885 to reduce or inhibit denaturation of the glucose isomerase during operation of the process is also contemplated.

It is necessary that the concentration of glucose in the glucose-containing feed liquor be within the range of from about 20 to about 65, and preferably from about 30 to about 50, weight percent if the desired results are to be achieved.

It is also necessary that the isomerization be carried out at a pH within the range of from about 3.0 to about 8.0 more preferably within the range of from about 4.0 to about 7.0 and most preferably between 5.0 and 6.5. Operation of the isomerization significantly below or above the aforestated pH range will lead to the formation of excessive quantities of undesirable by-products such as psicose, organic acids, colored products, color precursors, fructose dianhydrides and the like.

Yet another necessary requirement of the present invention lies in the duration of contact of the glucose-containing feed liquor and glucose isomerase. Such contact must be maintained within the range of from about 10 seconds to about 5 hours, preferably from about 30 seconds to about one hour and most preferably from about two minutes to about 30 minutes to provide fructose syrup of acceptable quality.

The preferred contact time between the glucose isomerase and the glucose containing liquor depends to a large extent upon the pH at which the isomerization reaction is conducted. At the lower end of the pH range, longer contact time can be tolerated without causing undue degradation of glucose and fructose through formation of psicose and other undesirable degradation products. At the upper end of the range, shorter contact time is necessary to avoid psicose and color formation. In practice, the total time the glucose containing syrup is at or near the final reaction temperature is reckoned as the effective contact time since the sugar degradation reactions which occur are nonenzymatic and take place whether or not the liquor is in contact with the glucose isomerase. Therefore, in conducting isomerizations above 90° C. it is important to minimize the time required to bring the glucose liquor to the desired isomerization temperature (as for example, by mixing the liquor with steam just before or during contact with the isomerase) and once the desired fructose level has been achieved to thereafter rapidly separate the liquor from any active isomerase and then cool the liquor as quickly as possible to less than 90° C. and preferably to less than 70° C. If a soluble form of glucose isomerase is used it will be necessary to inactivate such (as for example, by pH reduction to a range that will inactivate the isomerase) before the cooling step to avoid any reconversion to glucose of the fructose formed during the high temperature isomerization step since the isomerization reaction is, of course, reversible.

The maximum degree of conversion of glucose to fructose that can be attained is governed by the thermodynamic equilibrium between glucose and fructose which in turn is dependent upon the temperature at which the isomerization is conducted. Very careful analysis of equilibrium mixtures of glucose and fructose has established the following relationship.

$$F = 41.5 + 0.157\ T \tag{1}$$

where F is the % fructose at equilibrium based on total weight of glucose and fructose and T is the temperature (° C.) at which isomerization is conducted.

Contact time between the glucose containing syrup and isomerase in a reactor can generally be reckoned by reference to the following formula when a reactor containing an immobilized form of isomerase is used.

$$t = \frac{CV \ln \frac{F_e - F_o}{F_e - F}}{kA} \tag{2}$$

where
 t = the contact time
 C = concentration of glucose and fructose
 V = The free volume of fluid in the packed bed (volume of bed minus the volume occupied by the immobilized enzyme particles)
 $F_e$ = fraction of fructose in the glucose/fructose mixture at equilibrium when at the isomerization temperature
 $F_o$ = fraction of fructose (based on G+F) at the entrance to the packed bed
 F = fraction of fructose (based on G+F) in the solution exiting the packed bed
 k = reaction rate constant for isomerization at the isomerization conditions
 C = concentration of glucose and fructose in solutions
 A = activity of isomerase in the packed bed Values of k for immobilized isomerase prepared according to the examples following range from about 0.15 to about 5 g hr$^{-1}$ IGIU$^{-1}$ at temperatures from 90° C. to 130° C. respectively. This relationship shows the need to minimize contact time at high temperature by using packed beds of high activity per unit volume. Packed beds formed according to the procedures in the following examples can contain up to 2000 IGIU/ml which can result in attainment of 99.5% of equilibrium fructose content in a high temperature reactor in less than one minute when staged reactors are used at different temperatures and the feed to a first reactor is isomerized at low temperature before isomerizing at high temperature in a second reactor. Therfore, use of high potency packed beds can lead to very low effective contact times which in turn minimizes the degradation of fructose which occurs at the high temperatures required for this invention.

In commercial practice, however, fructose containing syrups are not manufactured from pure glucose. Rather, starch hydrolysates (as prepared in the above mentioned references) are used as the glucose source and these invariably contain non-glucose and non-fructose saccharides (hereinafter referred to as polysaccharides) derived from incomplete hydrolysis of starch, and the reversion of glucose. Typically these constitute from 3% to 8% of the total dry weight as the saccharides derived by starch hydrolysis. It is therefore necessary when reckoning the temperature at which isomerization is to be conducted to allow for any polysaccharide contained in the glucose liquor as well as other factors such as the total dry basis fructose content to be attained, formation of psicose and other nonglucose and nonfructose products during the effective contact time of the glucose liquor and the isomerase. Relationships for the calculation of isomerization temperature are shown below:

$$T = \frac{E - 41.5}{0.157} \tag{3}$$

$$E = \frac{10,000\ (M + C)}{Q(100 - P)} \tag{4}$$

T = isomerization temperature (° C.).
E = equilibrium fructose content (% based on total glucose + fructose) at temperature T.
M = % fructose dry basis required in the isomerized product.
C = % psicose + other degradation products formed during the effective isomerization contact time.
Q = % of equilibrium attained during isomerization reaction.
P = % polysaccharide content of glucose liquor.

Typically, less than 1% and preferably less than 0.5% psicose and other degradation products will be formed and 99.5% of equilibrium can be attained. Therefore, to prepare syrups with 55.5% fructose (dry basis), the following isomerization temperatures are required for glucose liquors of the indicated polysaccharide contents.

| Polysaccharide in Glucose liquor (% dry basis) | Isomerization Temperature (°C.) |
| --- | --- |
| 0 | 94.7 |
| 1 | 98.3 |
| 2 | 102.0 |
| 3 | 105.8 |
| 4 | 109.7 |
| 6 | 117.6 |
| 8 | 126.0 |

The accepted article of commerce contains on the average, 55.5% fructose on a dry basis. This is so because at this fructose level, high fructose corn syrup (HFCS) attains equal sweetness with sucrose on a weight for weight dry basis. Moreover, HFCS of 55.5% fructose content is firmly established as the article of commerce that is used interchangably as a total or partial replacement for sucrose in many food products and especially in carbonated soft drinks. Consumption of this type of HFCS in the U.S. is expected to be 2.9 billion pounds in 1982 with growth to 4.0 billion pounds in 1983. Owing to the complexities inherent in delivering, storing, metering and formulating HFCS into food products, there is a universal demand for uniformity of product from one HFCS manufacturer to another so that product from different supply sources can be used interchangably and simultaneously. Therefore, fructose level of 55-56% dry basis has attained special significance as a target level in the technology associated with HFCS manufacture.

The present process provides fructose levels of at least 53%, preferably at least 54% and most preferably at least 65%.

With the foregoing requirements of glucose concentration, pH and contact time in mind, known glucose isomerization processes can be suitably adapted to operate at from about 90° to about 130° C. to provide the high glucose-fructose syrups of this invention.

The following examples are further illustrative of the process of this invention.

EXAMPLE 1

This example shows direct isomerization of glucose at high temperature to attain a composition containing 55.5% fructose on a dry basis wherein a two stage isomerization system is used.

Soluble glucose isomerase was prepared by a method similar to that described in U.S. Pat. No. 3,788,945.

A species of *Streptomyces rubigenosus* derived from *S. rubigenosus* ATCC 21175 was grown by submerged aerobic fermentation on a medium with the following composition:

| | % by Wt. |
|---|---|
| Dextrose | 9.0 |
| Corn steep Liquor (Solids) | 1.6 |
| Diammonium Phosphate | 0.08 |
| Manganese Sulfate | 0.06 |
| Antifoam (Pluronic PL-61) | 0.003 |

The medium was sterilized at 121° C. for 45 min. cooled and adjusted to pH 6.8–7.0. It was inoculated with 14% (v/v) of an inocula comprising the contents of a seed fermenter prepared with the *S. rubigenosus* variant mentioned above. Fermentation was conducted under aseptic conditions at 30° C. for about 60 hours with aeration at 0.65 vvm. *S. rubigenosus* ATCC 21175 can also be used for inoculation and production of isomerase in which case media of the following composition are used.

| | |
|---|---|
| Dextrose | 0.24 |
| Corn Steep Liquor (solids) | 1.5 |
| Sorbitol | 1.6 |
| CoCl$_2$ | 0.02 |
| Diammonium Phosphate | 0.56 |
| Xylose | 1.0 |

Glucose isomerase was extracted from the *S. rubigenosus* by adding 0.35% Maquat MC 1412 (Mason Chemical Co.), and 10 ppm of hen's egg lysozyme and agitating for 5 hrs. at 40° C., pH 6.3–6.6. The mixture was then filtered to provide a solution of crude, unpurified glucose isomerase.

The crude isomerase was purified by adsorption on DEAE-cellulose (made according to U.S. Pat. No. 3,823,133), filtering and washing the adsorbed product with 0.1 M NaCl solution to remove impurities and then desorbing by contacting with 0.45 M NaCl solution. The pH of all solutions was maintained at 7.5 during the purification steps. The solution of partially purified isomerase obtained thereby was mixed with 3 volumes of 95% ethanol at 0° C. to precipitate the isomerase. Perlite filter acid was added, the solids recovered by filtration and air dried to provide a soluble isomerase preparation containing 2500 IGIU/g. Specific activity of the isomerase preparation was 40 IGIU/mg of protein.

A low temperature (70° C.) isomerase reactor was prepared by packing immobilized isomerase prepared according to U.S. Pat. No. 3,788,945 in a 1" dia. glass column to provide a bed 5 cm in height containing 20,000 IGIU of activity. The headspace over the packed bed contained a thermometer plus glass beads to minimize dead volume as far as possible. The column was fitted with inlet and outlet and was jacketed for circulation of water from a thermostat.

A high temperature (93°) reactor was prepared in the same manner using an immobilized isomerase obtained by adsorption of the purified isomerase described above on DEAE-cellulose. The packed bed contained 97,000 IGIU and was 15 cm in height.

Activity of the soluble isomerase preparation was determined as described by Lloyd et al. in Cereal Chemistry, 49, No. 5, pp. 544–553 (1972). One IGIU is the amount of isomerase that converts 1 micromole of glucose to fructose per minute in a solution containing 2 moles of glucose per liter, 0.02 moles of MgSO$_4$ per liter, and 0.001 moles of CoCl$_2$ per liter at a pH of 6.85 (0.2 M sodium maleate) and a temperature of 60° C. when determined by the above method.

A glucose containing solution was prepared by dissolving crystaline glucose (Clintose A granulation, Clinton Corn Processing Co.) in demineralized water to provide a solution containing 48% dry substance by weight. Activator and stabilizer substances were dissolved in the glucose solution to provide 25 mM sodium metabisulfite, 5 mM magnesium sulfate, and 0.1 mM cobalt chloride. The solution was adjusted to pH 6.8 with sodium hydroxide.

A first low temperature isomerization was conducted at 70° C. by pumping the above glucose solution through the low temperature reactor at 3.7 ml/min. The first 2500 ml of solution exiting the reactor were discarded and the effluent exiting the reactor thereafter collected for use in a second high temperature isomerization. In the high temperature isomerization, the solution obtained by isomerization at 70° C. was pumped through the high temperature reactor prepared as described above at 5 ml/min while maintaining the reactor temperature at 93° C. Contact time of solution in the high temperature reactor with the immobilized enzyme was about 12 minutes. Total time that the solution was at 93° C. inside the reactor was about 18 min. The solution was cooled in an ice bath immediately on exiting the high temperature reactor and the pH adjusted to 4.0. Effluent collected from the high temperature reactor during the first hour was discarded.

Isomerized glucose solutions obtained from the 70° C. and the 93° C. reactors were analyzed for carbohydrate composition and color and the results are compared with like analysis conducted on the unisomerized glucose solution as shown in Table 1.

TABLE 1

Composition of glucose solution isomerized at 70° C. and 93° C.

| Solution Treatment | Carbohydrate Composition (% by weight on an ash free dry basis) | | | | Color (CIRF X100) |
|---|---|---|---|---|---|
| | Fructose | Glucose | Psicose | Polysaccharide | |
| Unisomerized | 0 | 99.6 | 0 | 0.4 | 0.6 |
| Isomerized at 70° C. | 52.3 | 47.3 | 0.1 | 0.4 | 2.1 |

TABLE 1-continued

Composition of glucose solution isomerized at 70° C. and 93° C.

| Solution Treatment | Carbohydrate Composition (% by weight on an ash free dry basis) | | | | Color (CIRF X100) |
|---|---|---|---|---|---|
| | Fructose | Glucose | Psicose | Polysaccharide | |
| Isomerized at 93° C. | 55.5 | 43.7 | 0.4 | 0.4 | 4.8 |

The results show that 55.5% fructose was attained while maintaining psicose below 0.5% by weight dry basis. Color increase was less than 20 (CIRX×100).

Carbohydrate content was determined by method E-61 and color by method F-14 of the Standard Analytical Methods of the Member Companies of the Corn Refiners Association, Corn Refiners Association, Inc.; 1001 Connecticut Avenue, Washington, D.C. 20036. The color values obtained by method F-14 are multipled by 100 and are reported as (CIRF×100).

EXAMPLE 2

This example illustrates the preparation of a fructose containing product with 55.2% fructose prepared from a glucose containing solution comprising predominantly a refined corn starch hydrolysate.

The hydrolysate was prepared from corn starch by a process as described in U.S. Pat. No. 3,644,126 (liquefaction) and U.S. Pat. No. 3,280,006 (saccharification). The saccharified liquor was refined according to U.S. Pat. No. 3,834,940 to yield a product containing 95.3% glucose dry basis at 50% total dry substance. Sufficient crystalline glucose was added to bring the total glucose content to 97.1% on a dry basis. A solution was prepared from this with the following composition.

| | |
|---|---|
| Total Dry Substance (%) | 42.4 |
| Glucose (% Dry Basis) | 97.1 |
| Fructose (% Dry Basis) | 0.1 |
| Polysaccharide (% Dry Basis) | 2.8 |
| Psicose (% Dry Basis) | 0.0 |
| NaHSO$_3$ (mM) | 50 |
| MgSO$_4$ (mM) | 5 |
| CoCl$_2$ (mM) | 0.1 |
| pH | 6.8 |

A high temperature reactor was prepared as described in Example 1 containing 147,500 IGIU in a bed 16.5 cm. high. Temperature was controlled at 97.4° C. The above solution was pumped through the packed bed at 2.2 ml/min. The first 50 ml of effluent from the reactor was discarded and the effluent emanating from the column thereafter was sampled for analysis. Results are shown below versus the composition of the unisomerized glucose solution.

TABLE 2

| Solution Treatment | Carbohydrate Composition (% by weight on an ash free dry basis) | | | | Color (CIRF X100) |
|---|---|---|---|---|---|
| | Fructose | Glucose | Psicose | Polysaccharide | |
| Unisomerized | 0.1 | 97.1 | 0 | 2.8 | 0.6 |
| Isomerized at 97.4° C. | 55.2 | 42.4 | 0.2 | 2.2 | 12.4 |

The results show that greater than 55% fructose was attained with only 0.2% psicose formation. The higher color formed in this example was due to the fact that the entire isomerization was carried out at high temperature (97.4%) as opposed to the two stage process of Example 1 wherein most of the fructose was formed at a lower temperature (i.e., 70° C.) and could have been avoided by use of a two stage reactor. Nevertheless, color formed was less than 20 (CIRF×100).

We claim:

1. A process for isomerizing glucose to fructose which comprises contacting a glucose-containing feed liquor containing from about 20 to about 65 weight percent glucose with glucose isomerase at a temperature of from about 90° C. to about 130° C. at a pH of from about 3.5 to about 8 and a contact time of from about 10 seconds to about 5 hours to convert at least about 53 to about 60 weight percent of the glucose present in said liquor to fructose with no substantial formation of psicose and/or other non-fructose, non-glucose sugars with the product fructose-glucose syrup.

2. The process of claim 1 wherein the glucose-containing liquor is obtained from the hydrolysis of corn starch.

3. The process of claim 1 wherein the glucose isomerase is obtained from a microorganism selected from the group consisting of Streptomyces species, mutants, variants and genetic modifications thereof.

4. The process of claim 1 wherein the glucose isomerase is obtained from a microorganism selected from the group consisting of Streptomyces sp. ATCC 21175; mutants, variants, and genetic modifications thereof.

5. The process of claim 1 wherein the glucose isomerase is obtained from a microorganism into which a mutated glucose isomerase gene has been introduced said mutated gene providing glucose isomerase of high thermal stability.

6. The process of claim 1 wherein the glucose isomerase is a thermally stable glucose isomerase.

7. The process of claim 6 wherein the thermally stable glucose isomerase is obtained from *Bacillus stearothermophilus*.

8. The process of claim 6 wherein the thermally stable glucose isomerase is obtained from *Bacillus licheniformis*.

9. The process of claim 6 wherein the thermally stable glucose isomerase is obtained from a thermophile of the genera Thermoactinomyces, Thermopolyspora, Thermomonospora or Pseudonocardia.

10. The process of claim 6 wherein the thermal stable glucose isomerase is obtained from a microorganism of the genus Ampullariella.

11. The process of claim 1 wherein an enzyme denaturation-inhibiting amount of water soluble salt of sulfurous acid is present in the isomerization medium.

12. The process of claim 1 wherein the glucose-containing feed liquor contains from about 30 to about 50 weight percent glucose.

13. The process of claim 1 wherein the glucose-containing feed liquor is contacted with glucose isomerase at about 95° C. to about 105° C.

14. The process of claim 1 wherein the pH of the isomerization medium is maintained at about 5 to about 6.5.

15. The process of claim 1 wherein the contact time is from about 2 minutes to about 30 minutes.

16. The process of claim 1 wherein the glucose isomerase is used in the immobilized form.

17. The process of claim 14 wherein the glucose isomerase is immobilized upon diethylaminoethyl cellulose.

18. A process for enzymatically converting glucose to fructose which comprises contacting a glucose-containing feed liquor containing from about 20 to about 65 weight percent glucose with glucose isomerase at a temperature of from about 20° C. to about 80° C. at a pH of about 6.0 to 9.0 and a contact time of about one to about 2 hours to convert from 40 to about 45 weight percent of the glucose present in said liquor to fructose, increasing the temperature of the isomerization medium to from about 90° C. to about 130° C., adjusting the pH of the isomerization medium as necessary to within the range of from about 3 to about 8, contacting the fructose-containing liquor with the glucose isomerase for an additional period of from about 10 seconds to about 5 hours to increase the conversion level to from about 53 to about 60 weight percent of the glucose present in the original glucose-containing feed liquor and thereafter cooling the product fructose-glucose syrup to a temperature of from about 20° C. to about 80° C., there being no substantial formation of psicose or other non-fructose, non-glucose sugars.

19. The process of claim 18 wherein the glucose-containing liquor is obtained from the hydrolysis of corn starch.

20. The process of claim 18 wherein the glucose isomerase is obtained from Streptomyces sp. ATCC 21175.

21. The process of claim 18 wherein the glucose isomerase is a thermally stable glucose isomerase.

22. The process of claim 21 wherein the thermally stable glucose isomerase is obtained from *Bacillus stearothermophilus*.

23. The process of claim 21 wherein the thermally stable glucose isomerase is obtained from *Bacillus licheniformis*.

24. The process of claim 21 wherein the thermally stable glucose isomerase is obtained from a thermophile of the genera Thermoactinomyces, Thermopolyspora, Thermomonospora or Pseudonocardia.

25. The process of claim 21 wherein the thermally stable glucose isomerase is obtained from a microorganism of the genus Ampullariella.

26. The process of claim 18 wherein an enzyme denaturation-inhibiting amount of water soluble salt of sulfurous acid is present in the isomerization medium.

27. The process of claim 18 wherein the glucose-containing feed liquor contains from about 30 to about 50 weight percent glucose.

28. The process of claim 18 wherein the fructose-containing liquor resulting from the initial contacting step is further contacted with glucose isomerase at about 95° C. to about 105° C.

29. The process of claim 18 wherein the pH of the isomerization medium following the initial contact step is adjusted to and maintained at about 5.5 to about 6.0.

30. The process of claim 18 wherein the glucose isomerase is used in the immobilized form.

31. The process of claim 30 wherein the glucose isomerase is immobilized upon diethylaminoethyl cellulose.

32. A process for isomerizing glucose to fructose which comprises contacting a glucose-containing feed liquor containing from about 20 to about 65 weight percent glucose with glucose isomerase at a temperature of from about 90° C. to about 130° C. at a pH of from about 3.5 to about 8 and a contact time of from about 10 seconds to about 5 hours to convert at least about 53 to about 60 weight percent of the glucose present in said liquor to fructose with no substantial formation of psicose and/or other non-fructose, non-glucose sugars with the product fructose-glucose syrup and thereafter cooling the reaction mixture to a temperature below 80° C. after the enzyme has been removed from contact with the reaction mixture.

33. The process of claim 32 wherein the glucose containing feed liquor is contacted with glucose isomerase at a temperature of from about 95° C. to about 105° C.

34. The process of claim 32 wherein the pH of the medium is maintained at about 5 to about 6.5.

35. The process of claim 32 wherein the contact time is from 2 minutes to 30 minutes.

36. A process for enzymatically converting glucose to fructose which comprises contacting a glucose-containing feed liquor containing from about 20 to about 65 weight percent glucose with glucose isomerase at a temperature of from about 20° C. to about 80° C. at a pH of about 6.0 to 9.0 and a contact time of about one to about 2 hours to convert from 40 to about 45 weight percent of the glucose present in said liquor to fructose, increasing the temperature of the isomerization medium to from about 90° C. to about 130° C., adjusting the pH of the isomerization medium as necessary to within the range of from about 3 to about 8, contacting the fructose-containing liquor with the glucose isomerase for an additional period of from about 10 seconds to about 5 hours to increase the conversion level to from about 53 to about 60 weight percent of the glucose present in the original glucose-containing feed liquor and thereafter cooling the product fructose-glucose syrup to a temperature of from about 20° C. to about 80° C., there being no substantial formation of psicose or other non-fructose, non-glucose sugars and thereafter cooling the reaction mixture to a temperature below 80° C. after the enzyme has been removed from contact with the reaction mixture.

37. The process of claim 36 wherein the glucose containing feed liquor is contacted with glucose isomerase at a temperature of from about 95° C. to about 105° C.

38. The process of claim 36 wherein the pH of the medium is maintained at about 5 to about 6.5.

39. The process of claim 36 wherein the contact time is from 2 minutes to 30 minutes.

* * * * *